United States Patent [19]

Crowther et al.

[11] Patent Number: 5,593,432
[45] Date of Patent: Jan. 14, 1997

[54] METHOD FOR NEUROSTIMULATION FOR PAIN ALLEVIATION

[75] Inventors: Gordon H. Crowther, deceased, late of Los Angeles County; by Donn Younce, executor, Oxnard, both of Calif.

[73] Assignee: Neuroware Therapy International, Inc., Pasadena, Calif.

[21] Appl. No.: 81,977

[22] Filed: Jun. 23, 1993

[51] Int. Cl.⁶ .................................................... A61N 1/00
[52] U.S. Cl. .............................................. 607/46; 607/58
[58] Field of Search ................................. 607/45, 46, 72, 607/76, 58

[56] References Cited

U.S. PATENT DOCUMENTS 4,232,680  11/1980  Hudleson et al. ..................... 607/46
4,646,744  3/1987  Capel ..................................... 607/46
4,865,048  9/1989  Eckerson .............................. 607/46
4,924,880  5/1990  O'Neill ................................. 607/76

*Primary Examiner*—William E. Kamm
*Assistant Examiner*—Scott M. Getzow
*Attorney, Agent, or Firm*—J. E. Brunton

[57] ABSTRACT

A method and apparatus for alleviating pain and the symptoms of withdrawal of a patient during detoxification. The apparatus generates and applies to the patient's mastoid processes a multiplicity of current controlled electrical pulses comprised of generally square waves having a pulse width of about 200 microseconds. The pulse repetition rate varies between about 10 and 2000 Hertz and programmed treatment spans periods of up to ten days.

3 Claims, 3 Drawing Sheets

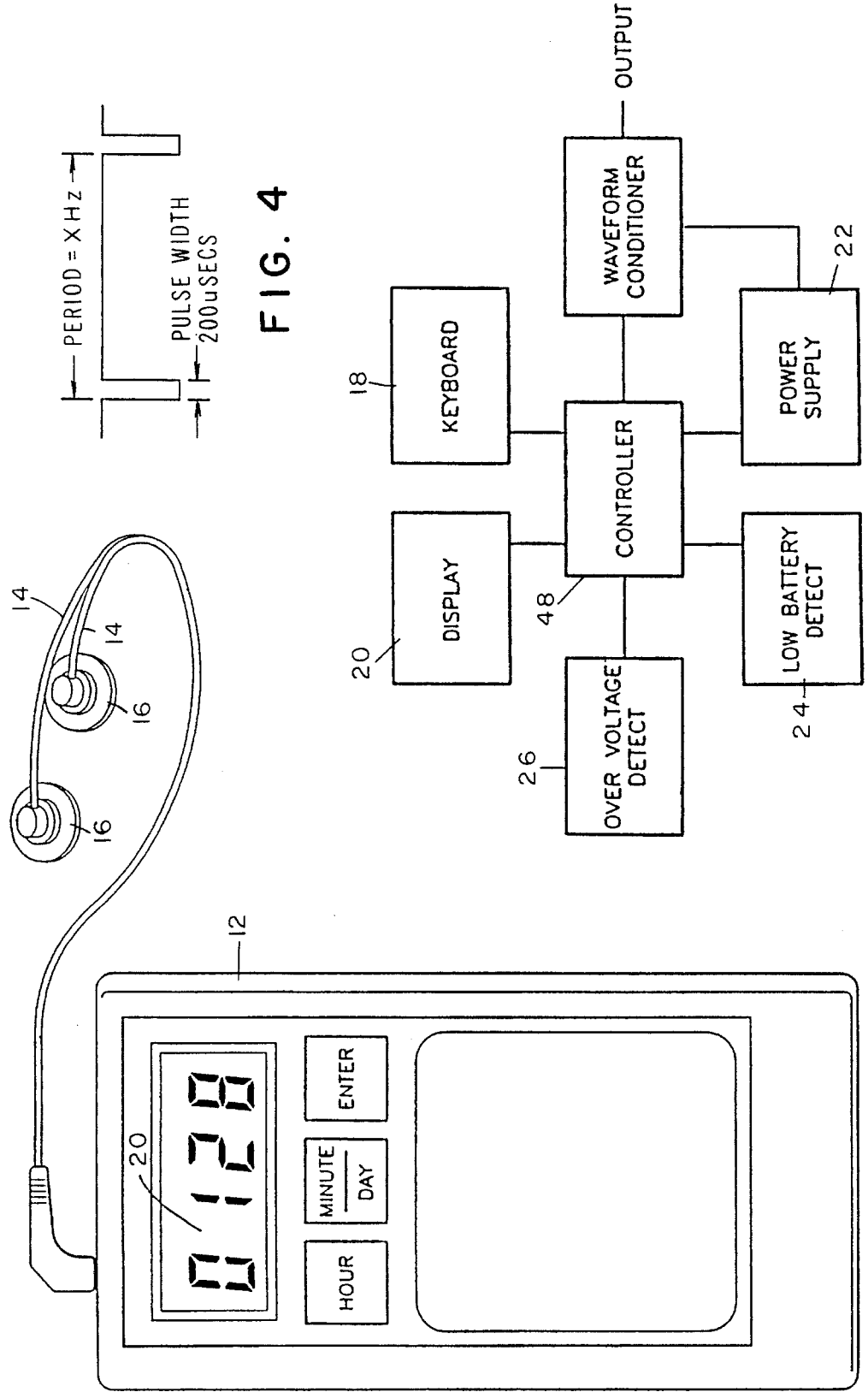

METHOD FOR NEUROSTIMULATION FOR PAIN ALLEVIATION

BACKGROUND OF THE INVENTION

1. Field of the Invention

The present invention relates generally to a method and apparatus for stimulating the nervous system. More particularly, the invention concerns a method and apparatus for neurostimulation that assists in the relief of pain and drug addiction withdrawal symptoms during detoxification.

2. Discussion of the Invention

A growing problem in the United States and in many parts of the world is drug and alcohol addiction. Solutions to this widespread problem are desperately needed. A major element of any such solution is a meaningful method of effectively detoxifying the addict to expedite a return to a productive life.

The most commonly used detoxification method at the present time involves the use of methadone. Methadone acts as a drug substitute during the treatment period and helps to assist the patient through the withdrawal state which in many cases is extremely traumatic. The biochemical basis of addiction is believed to involve the body's natural pain killers which are secreted by the brain into the nervous system. These pain killers are generally referred to as endorphins and enkephalins and are believed to be involved in all addictive behaviors including alcoholism, smoking and compulsive overeating. More particularly, endorphins are proteins having potent analgesic properties that naturally occur in the brain. Enkephalins, on the other hand, are pentapeptides with opiate and analgesic activity that occur naturally in the brain. The acute withdrawal symptoms of the addict is believed directly associated with low levels of endorphins within the body and altered ratios of different kinds of endorphins and enkephalins within the body which has been caused by previous involvement with drugs of addiction. The ingestion of methadone into the body acts as a drug substitute and tends to alleviate the acute withdrawal symptoms experienced by the addict. A major problem with methadone treatment, of course, is that eventually the patient must also be weaned from the methadone, which itself results in serious withdrawal symptoms.

It is generally accepted that the most acute withdrawal symptoms are associated with the somatosensing nervous system. This system senses pain and the general well being of the body. Withdrawal symptoms associated with the somatosensing nervous system include muscle cramps and severe pain in the body joints.

A major thrust of the present invention is to provide treatment that effectively helps alleviate the patient's withdrawal symptoms, including those associated with the somatosensory nervous system. This is achieved through neurowave therapy and is accomplished by connecting small probes to the patient at strategic locations for the delivering of a preprogrammed sequence of electrical pulses over an extended period of time.

In the past, a number of crude electrical devices have been developed and marketed as electronic acupuncture devices. For the most part, these device have little medical value and merely deliver some type of arbitrary electrical pulse to the patient at selected "acupuncture points". A much more sophisticated device is described in U.S. Pat. No. 4,965,048 issued to Eckerson. However, the Eckerson device, unlike that of the present invention, delivers to the patient a train of electrical pulses comprised of square waves and spikes of specifically defined pulse width and amplitude. More particularly, the Eckerson device applies a train of electrical pulses that consist of individual pulses having an amplitude of 20 volts and a pulse width of one millisecond, followed immediately by a voltage spike of opposite polarity with an amplitude of 70 volts.

As will become more apparent from the discussion which follows, the method and apparatus of the present invention is significantly different in many respects from that of Eckerson. By way of example, the device of the present invention does not apply electrical pulses that include spikes and the wave form uniquely maintains a constant current instead of a specific voltage. Additionally, unlike the Eckerson device, the device of the present invention does not permit the user to vary the frequency of the pulses but, rather, advantageously employs a microprocessor based circuit for precise sequencing and wave form generation.

SUMMARY OF THE INVENTION

It is an object of the present invention to provide a novel drug-free method and apparatus for use in the relief of pain and in the alleviation of acute drug and alcohol withdrawal symptoms.

More particularly, it is an object of the invention to provide a compact, readily portable device having non-invasive skin probes that deliver a preprogrammed sequence of electrical pulses that can be specifically programmed over elongated time periods to relieve a variety of different types of pain.

Another object of the invention is to provide a method and apparatus of the aforementioned character that functions by electrostimulation to promote the increase in production of endorphins within the body.

Another object of the invention is to provide a device of the character described that is easy and safe to use and requires minimal supervision by physicians and health care providers.

Still another object of the invention is to provide a device that is rugged, highly reliable in use and one that requires minimum care and maintenance.

Another object of the invention is to provide an apparatus that delivers constant current output pulses that are controllably generated by a constant current amplifier.

Another object of the invention is to provide a method that stimulates the brain cells to replace endorphins which may have been altered, or reduced in number as a result of drug addiction by the patient.

Yet another object of the invention is to provide a method of providing to the patient up to a ten-day preprogrammed sequence of electrical pulses that can be specifically programmed to relieve the patient of a particular type of pain.

BRIEF DESCRIPTION OF THE DRAWINGS

FIG. 1 is a generally perspective view of one form of the therapy device of the present invention.

FIG. 2 is a generally diagrammatic block diagram of the device of FIG. 1 illustrating unit function.

FIG. 4 is a diagrammatic illustration of the output wave form of the apparatus of the device.

DESCRIPTION OF THE INVENTION

Figure 3:
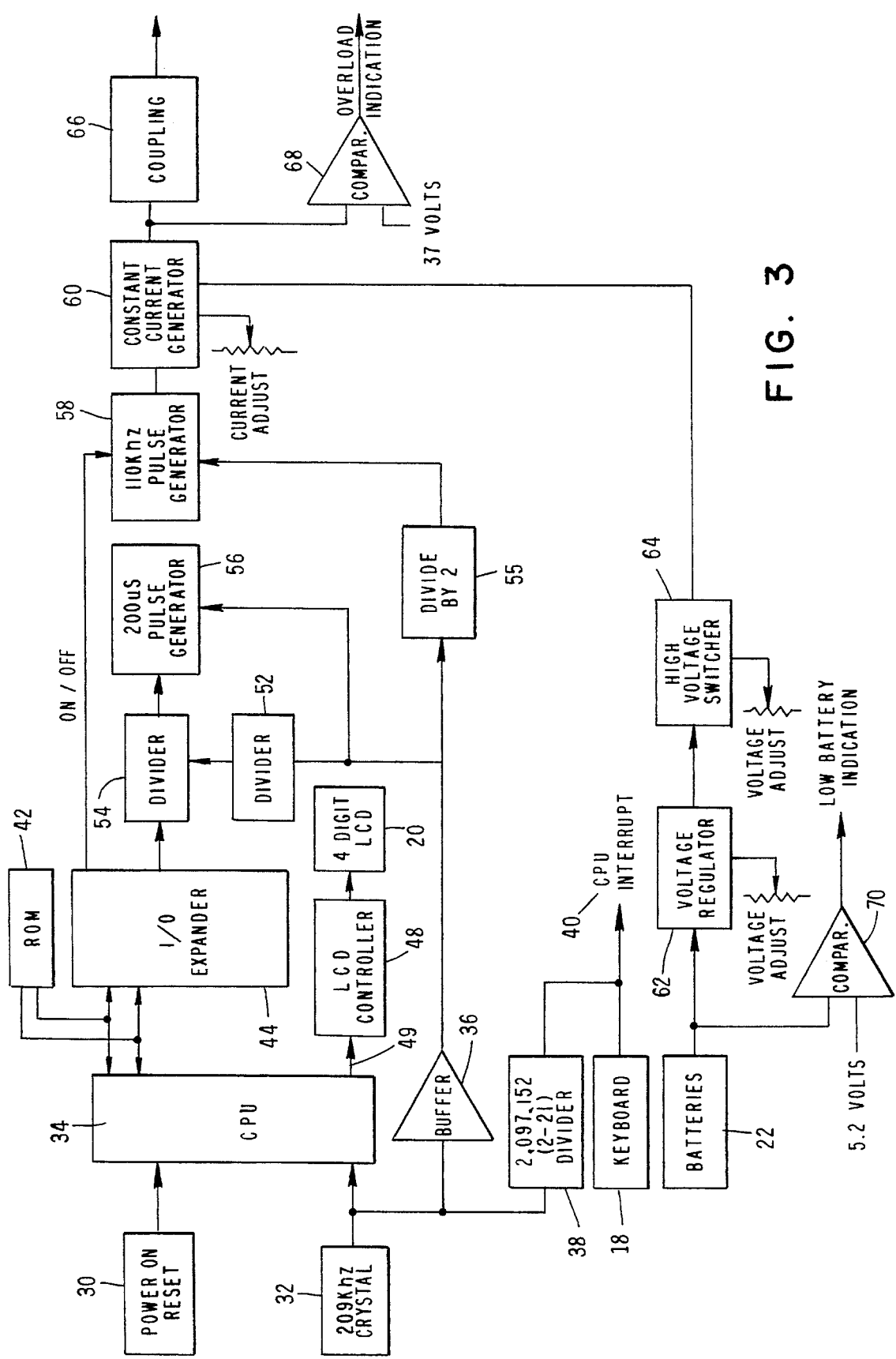
FIG. 3 is a generally schematic view of the internal circuitry of the therapy device.

Referring to the drawings and particularly to FIGS. 1 and 2, one form of the device of the present invention comprises a compact, hollow casing 12 which is adapted to house the electrical circuitry of the device the character which will presently be described. Electrically connected to the circuitry housed within casing 12 via electrical wires or connectors 14 are electrostimulation means for providing electrical pulses to the patient. These means are here provided as a pair of skin probes 16 which can be placed in contact with the patient's body at selected locations as, for example, proximate the patient's mastoid processes.

A keyboard 18 (FIG. 2) is provided for entering the time and day at which the sequence which has been pre-programmed in the computer is to commence. A four digit LCD display 20 shows the program time and also displays the condition of the batteries which are preferably also disposed within casing 12 and which comprise the power supply 22 of the device. (See also low battery detect 24 in FIG. 2). The replaceable batteries of the device, which comprise the power source, are selected so as to provide power to the circuit for at least a full ten-day program sequence the character of which will be described hereinafter. Many such batteries are readily commercially available and their operation is well understood by those skilled in the art. Display 20 also functions to display an overload condition as maybe detected by the overvoltage detect 26 (FIG. 2).

Turning also to FIG. 3, wherein the details of the circuitry of the device is schematically shown, the power on reset 30 comprises a 4071 of the character manufactured and sold by SGS-Thomson located in Australia, Brazil, Canada, France, Germany, Hong Kong, Italy, Japan, Korea, Malaysia, Malta, Morocco, The Netherlands, Singapore, Spain, Sweden, Switzerland, Taiwan, United Kingdom and U.S.A. This input to the 4071 is a RC circuit of about 0.5 seconds. This construction permits the crystal 22 to start up and the logic supply voltage to reach its set point before resetting the central processing unit (CPU) 34. Crystal 32 which, like power on reset 30, is connected to CPU 34, is a crystal whose operating frequency is on the order of about 209.715 kHz. Crystal 32, which is commercially available from various suppliers such as Statek of Orange, Calif. provides the base operating frequency for the entire system.

Connected to crystal 32 is a buffer 36 and 2,097,152 divider 38. Divider 38 divides the operating frequency by 2 to the 21st power (2,097,152). This generates a square wave with a period of 10 seconds. The same chip has a buffered output of the original input which is used to drive the dividers which generate the output wave forms. Buffer 36 is available from suppliers such as SGS-Thomson of countries listed above. Divider 38 is also readily commercially available from suppliers such as SGS-Thomson of countries listed above. The previously identified keyboard 18 consists of 3 keys that are stroked by the CPU. The keyboard outputs are combined with the 10 second square wave input into the CPU interrupt 40. This provides the CPU with a 10 second real time interrupt and a keyboard service interrupt.

The CPU 34 is an 80C35 which is readily available from Intel of Santa Clara, Calif. and functions by means of appropriate software to control the unit in a manner well understood by those skilled in the art. The read-only memory (ROM) 42 which runs the CPU 35 is preferably a 87C64 which is also available from Intel of Santa Clara, Calif.

Interconnected with CPU 34 and ROM 42 is an I/O Expander 44 which is available from Intel of Santa Clara, Calif. and is sold under the designation 82C43. Expander 44 provides additional I/O ports that control the dividers and also turn on the high voltage to the unit.

The previously mentioned LCD display 20 is controlled by a U7225 LCD controllor 48 which is accessed by 6 I/O lines from the CPU which are depicted in FIG. 3 by the numeral 49.

Connected to I/O Expander 44 is a first stage divider shown here as a 40103 ripple counter 52 set in the divide mode. Counter 52 is programmed by the I/O expander that divides the 209 KHz signal, and it can be set to divide from 2 to 256. Ripple counter 52 is readily commercially available from sources such as SGS-Thomson of multiple countries listed above.

Also connected to I/O expander 44 and to divider 52 is a second stage divider, here provided as a 40103 ripple counter 54 which is set in the divide mode. Counter 54 is programmed by the I/O expander that divides the signal from the 1st stage divider and can be set to divide by 1,2,9, 27, 81, and 243. Counter 54 is also available from SGS.

Connected to divider 54 is a pulse generator shown here as a 40103 ripple counter 56 which is set in the one shot mode. When counter 56 is pulsed by the output from the 2nd stage divider 54 it outputs a pulse that is 200 micro seconds long.

A divide 2 device, here provided as a 4013 SR Flip Flop 56, is connected to divider 52 and buffer 36 in the manner shown in FIG. 3. Flip Flop 56 is configured to divide the input signal (209 Khz) by two. The output is appropriately fed into a 105 KHz pulse modulator 58 which is a combination of AND or OR gates that is set up, upon a signal from the I/O EXPANDER, to modulate the 200 uS output with 105 KHz. Pulse modulator 58 is of a character well known in the art and is available from several sources, including SGS-Thomson of multiple countries listed above.

Figure 5:
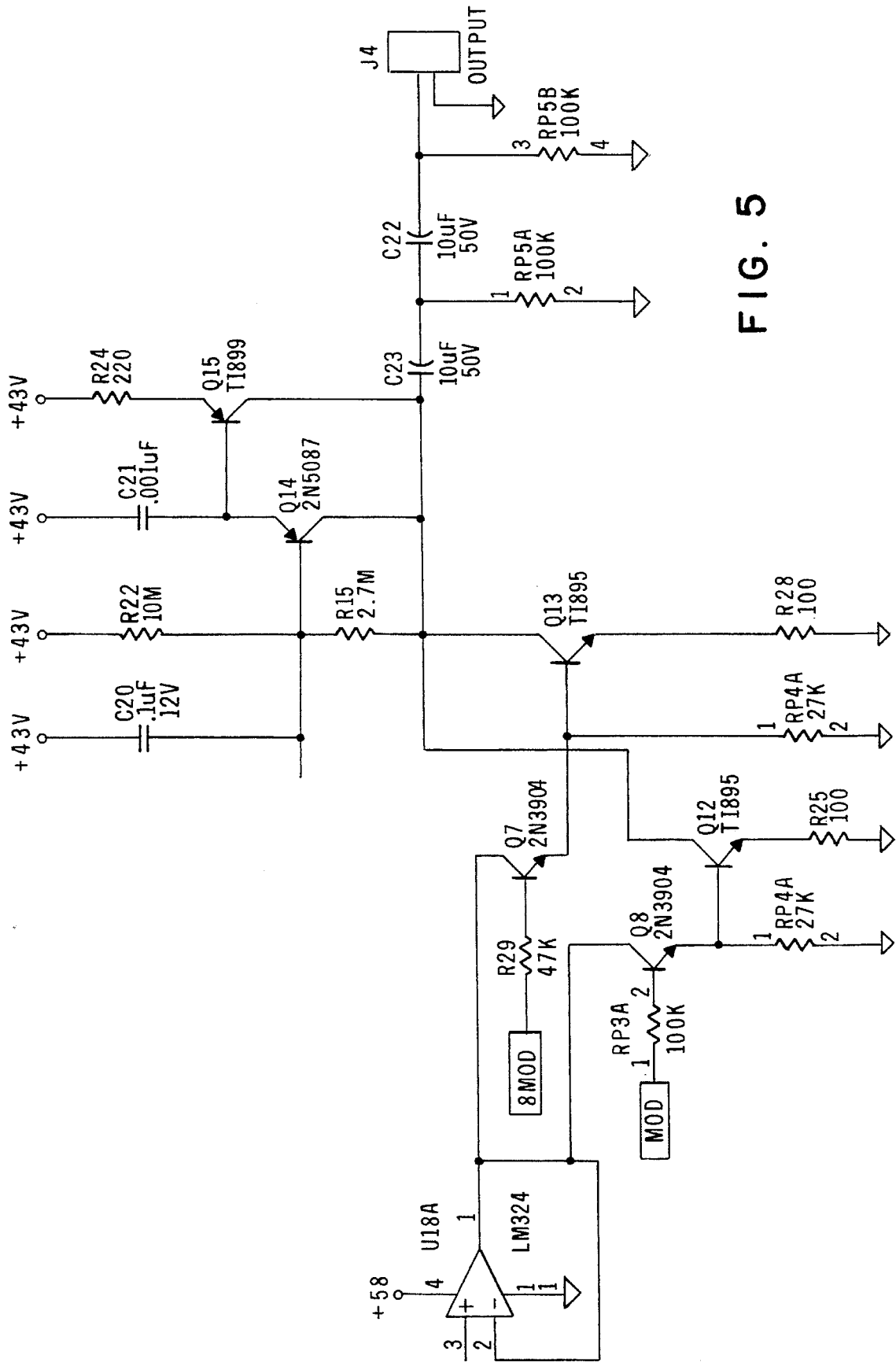
FIG. 5 is a generally schematic view of the constant current circuit of one form of the device of the invention.

Connected to pulse modular 58 is a constant current generator 60 which is, in turn, connected to the power supply or batteries 22, via a voltage regulator 62 and a high voltage switcher 64. The constant current circuit of the instant form of the invention is shown in FIG. 5. Referring to FIG. 5 it can be seen that the Pulse Current Generator, delivers the current to the load (Patient). The other, the Retrace Current Generator, sinks current from the load.

In practice, the operation of the Pulsed Current Generator is initiated when the transistors Q7 and Q8 are pulsed on and off by the microprocessor in order to provide the basic modulated pulse pattern. These drive the Darlington Amplifiers Q12 and Q13 which taken together provide a constant current pulse to the load. In order to insure that the net current to the load is equal to zero (no DC component), a Retrace Current Generator is provided by the Darlington pair Q15 and Q14. The average current in this amplifier is equal to the pulsed current.

With respect to the interaction of the current generators with the supply voltages, the following is to be observed. First, the stable voltage labeled +43 V is connected to the collectors of the Retrace Generator transistors. This circuit drops between 1 and 2 volts which establishes the voltage for the Pulse Generator required to provide the necessary current amplitude. The second supply voltage is the +6 V to the unity gain amplifier, U18 which allows the Pulsed Current Generator current to be set.

Connected to generator 60 is a coupling 66 which comprises a series of capacitors which couple the output of the current generator to deliver the current to the skin probes 16. An overvoltage comparator 68 is also connected to generator 60 and functions to indicate when wires have broken or the skin probe connections to the patient are becoming dry and ineffective.

Voltage regulator 62 comprises a ICL7663 of the character available from GE-Intersil of Cupertino, Calif. and functions to regulate the battery voltage (6.2–5.2 volts) to 3.8 volts.

Preferably the High Voltage switcher 64 consists of an adjustable switcher power supply that is readily commercially available and steps up the 3.8 volts to the 43 volts that is used by the constant current generator. Switcher 64 can conveniently be turned on and off by the CPU 34.

Associated with batteries 22 is a low battery comparator 70 which alerts the CPU when the battery voltage reaches a level less than 5.2 volts.

As previously mentioned, the apparatus of the invention is designed to deliver multiday preprogrammed sequences of electrical pulses that are specifically adapted to treat withdrawal symptoms from a number of additive drugs including heroin, cocaine, amphetamines, alcohol, synthetic pain killers and various stimulants and sedatives. Programs can also be designed to treat numerous types of pain, including chronic pain, post operative pain, pain from bodily injury and pain from arthritis.

The various specially designed programs of the present invention involve the use of wave forms of the character depicted in FIG. 4 wherein the pulse width is on the order of between about 100 and 300 microseconds and the period ranges from about 10 Hz to about 2000 Hz.

By way of example, in the conduct of one form of the method of the invention for treating withdrawal symptoms of heroin addicts and of users of synthetic pain killers, the following ten-day program is followed:

| Day | Freq. (Hz) | Time Interval |
| --- | --- | --- |
| 1 | 90 | 00:00–23:59 |
| 2 | 90 | 00:00–23:59 |
| 3 | 90 | 00:00–09:59 |
|   | 300 | 10:00–10:29 |
|   | 90 | 10:30–18:59 |
|   | 300 | 19:00–19:29 |
|   | 90 | 19:30–23:59 |
| 4 | 90 | 00:00–09:59 |
|   | 300 | 10:00–10:59 |
|   | 90 | 11:00–18:59 |
|   | 300 | 19:00–19:59 |
|   | 90 | 20:00–22:59 |
|   | 10/110 | 23:00–23:59 |
| 5 | 30/110 | 00:00–04:59 |
|   | 90 | 05:00–09:59 |
|   | 300 | 10:00–10:59 |
|   | 90 | 11:00–18:59 |
|   | 300 | 19:00–19:59 |
|   | 90 | 20:00–22:59 |
|   | 30/110 | 23:00–23:59 |
| 6 | 30/110 | 00:00–04:59 |
|   | 90 | 05:00–09:59 |
|   | OFF | 10:00–10:59 |
|   | 300 | 11:00–11:59 |
|   | 90 | 12:00–18:59 |
|   | OFF | 19:00–19:59 |
|   | 300 | 20:00–20:59 |
|   | 90 | 21:00–22:59 |
|   | 30/110 | 23:00–23:59 |
| 7 | 30/110 | 00:00–04:59 |
|   | 90 | 05:00–09:59 |
|   | OFF | 10:00–11:59 |
|   | 90 | 11:00–18:59 |
|   | OFF | 19:00–20:59 |
|   | 90 | 21:00–22:59 |
|   | 30/110 | 23:00–23:59 |
| 8 | 30/110 | 00:00–04:59 |
|   | 90 | 05:00–09:59 |
|   | OFF | 10:00–12:59 |
|   | 90 | 13:00–14:59 |
|   | 300 | 15:00–15:59 |
|   | 90 | 16:00–18:59 |
|   | OFF | 19:00–21:59 |
|   | 90 | 22:00–22:59 |
|   | 30/110 | 23:00–23:59 |
| 9 | 30/110 | 00:00–04:59 |
|   | OFF | 05:00–05:59 |
|   | 90 | 06:00–08:59 |
|   | OFF | 09:00–14:59 |
|   | 300 | 15:00–15:59 |
|   | OFF | 16:00–17:59 |
|   | 90 | 18:00–19:59 |
|   | OFF | 20:00–22:59 |
|   | 30/110 | 23:00–23:59 |
| 10 | 30/110 | 00:00–04:59 |
|   | OFF | 05:00–05:59 |
|   | 90 | 06:00–08:59 |
|   | OFF | 09:00–17:59 |
|   | 90 | 18:00–18:59 |
|   | OFF | 19:00–22:59 |
|   | 30/110 | 23:00–23:59 |

The program best suited for treating alcohol-related problems is as follows:

| Day | Freq. (Hz) | Time Interval |
| --- | --- | --- |
| 1 | 100 | 00:00–08:59 |
| 1 | 500 | 09:00–09:59 |
| 1 | 100 | 10:00–13:59 |
| 1 | 500 | 14:00–14:59 |
| 1 | 100 | 15:00–18:59 |
| 1 | 500 | 19:00–19:59 |
| 1 | 100 | 20:00–23:59 |
| 2 | 100 | 00:00–08:59 |
| 2 | 500 | 09:00–09:59 |
| 2 | 100 | 10:00–13:59 |
| 2 | 500 | 14:00–14:59 |
| 2 | 100 | 15:00–18:59 |
| 2 | 500 | 19:00–19:59 |
| 2 | 100 | 20:00–23:59 |
| 3 | 100 | 00:00–08:59 |
| 3 | 500 | 09:00–09:59 |
| 3 | 100 | 10:00–13:59 |
| 3 | 500 | 14:00–14:59 |
| 3 | 100 | 15:00–18:59 |
| 3 | 500 | 19:00–19:59 |
| 3 | 100 | 20:00–23:59 |
| 3 | 10/110 | 23:00–23:59 |
| 4 | 30/110 | 00:00–05:59 |
| 4 | 100 | 06:00–08:59 |
| 4 | 500 | 09:00–09:59 |
| 4 | 100 | 10:00–13:59 |
| 4 | 500 | 14:00–14:59 |
| 4 | 100 | 15:00–18:59 |
| 4 | 500 | 19:00–19:59 |
| 4 | 100 | 20:00–22:59 |
| 4 | 30/110 | 23:00–23:59 |
| 5 | 30/119 | 00:00–05:59 |
| 5 | 100 | 06:00–08:59 |
| 5 | 500 | 09:00–09:59 |
| 5 | 100 | 10:00–13:59 |
| 5 | 500 | 14:00–14:59 |
| 5 | 100 | 15:00–18:59 |
| 5 | 500 | 19:00–19:59 |
| 5 | 100 | 20:00–22:59 |
| 5 | 30/110 | 23:00–23:59 |
| 6 | 30/110 | 00:00–05:59 |
| 6 | 100 | 06:00–08:56 |
| 6 | 500 | 09:00–09:59 |
| 6 | OFF | 10:00–10:59 |

-continued

| Day | Freq. (Hz) | Time Interval |
|---|---|---|
| 6 | 100 | 11:00–13:59 |
| 6 | 500 | 14:00–14:59 |
| 6 | 100 | 15:00–17:59 |
| 6 | OFF | 18:00–18:59 |
| 6 | 500 | 19:00–19:59 |
| 6 | 100 | 20:00–22:59 |
| 6 | 30/110 | 23:00–23:59 |
| 7 | 30/110 | 00:00–05:59 |
| 7 | 100 | 06:00–08:56 |
| 7 | 500 | 09:00–09:59 |
| 7 | OFF | 10:00–11:59 |
| 7 | 100 | 12:00–13:59 |
| 7 | 500 | 14:00–14:59 |
| 7 | 100 | 15:00–18:59 |
| 7 | OFF | 19:00–20:59 |
| 7 | 500 | 21:00–21:59 |
| 7 | 100 | 22:00–22:59 |
| 7 | 30/110 | 23:00–23:59 |
| 8 | 30/110 | 00:00–05:59 |
| 8 | 100 | 06:00–08:59 |
| 8 | 500 | 09:00–09:59 |
| 8 | OFF | 10:00–12:59 |
| 8 | 100 | 13:00–13:59 |
| 8 | OFF | 14:00–14:59 |
| 8 | 100 | 15:00–15:59 |
| 8 | OFF | 16:00–18:59 |
| 8 | 500 | 19:00–19:59 |
| 8 | 100 | 22:00–22:59 |
| 8 | 30/110 | 23:00–23:59 |
| 9 | 30/110 | 00:00–05:59 |
| 9 | OFF | 06:00–06:59 |
| 9 | 100 | 07:00–08:59 |
| 9 | 500 | 09:00–09:59 |
| 9 | OFF | 10:00–13:59 |
| 9 | 500 | 14:00–14:59 |
| 9 | OFF | 15:00–18:59 |
| 9 | 500 | 19:00–19:59 |
| 9 | 100 | 20:00–20:59 |
| 9 | OFF | 21:00–22:59 |
| 9 | 30/110 | 23:00–23:59 |
| 10 | 30/110 | 00:00–05:59 |
| 10 | OFF | 06:00–06:59 |
| 10 | 100 | 07:00–08:59 |
| 10 | 50 | 09:00–09:59 |
| 10 | OFF | 10:00–18:59 |
| 10 | 500 | 19:00–19:59 |
| 10 | 100 | 20:00–20:59 |
| 10 | OFF | 21:00–22:59 |
| 10 | 30/110 | 23:00–23:59 |

By way of further example, the program found to be highly successful in relieving pain including chronic pain, and arthritis is as follows:

| Day | Freq. (Hz) | Time Interval |
|---|---|---|
| 1 | 30 | 00:00–08:59 |
| 1 | 500 | 09:00–09:59 |
| 1 | 30 | 10:00–13:59 |
| 1 | 500 | 14:00–14:59 |
| 1 | 30 | 15:00–18:59 |
| 1 | 500 | 19:00–19:59 |
| 1 | 30 | 20:00–23:59 |
| 2 | 30 | 00:00–08:59 |
| 2 | 500 | 09:00–09:59 |
| 2 | 30 | 10:00–13:59 |
| 2 | 500 | 14:00–14:59 |
| 2 | 30 | 15:00–18:59 |
| 2 | 500 | 19:00–19:59 |
| 2 | 30 | 20:00–23:59 |
| 3 | 30 | 00:00–08:59 |
| 3 | 500 | 09:00–09:59 |
| 3 | 30 | 10:00–13:59 |
| 3 | 500 | 14:00–14:59 |
| 3 | 30 | 15:00–18:59 |
| 3 | 599 | 19:00–19:59 |
| 3 | 30 | 20:00–22:59 |
| 3 | 30/110 | 23:00–23:59 |
| 4 | 30/110 | 00:00–05:59 |
| 4 | 30 | 06:00–08:59 |
| 4 | 500 | 09:00–09:59 |
| 4 | 30 | 10:00–13:59 |
| 4 | 500 | 14:00–14:59 |
| 4 | 30 | 15:00–18:59 |
| 4 | 500 | 19:00–19:59 |
| 4 | 30 | 20:00–22:59 |
| 4 | 30/110 | 23:00–23:59 |
| 5 | 30/110 | 00:00–05:59 |
| 5 | 30 | 06:00–08:59 |
| 5 | 500 | 09:00–09:59 |
| 5 | 30 | 10:00–13:59 |
| 5 | 500 | 14:00–14:59 |
| 5 | 30 | 15:00–18:59 |
| 5 | 500 | 19:00–19:59 |
| 5 | 30 | 20:00–22:59 |
| 5 | 30/110 | 23:00–23:59 |
| 6 | 30/110 | 00:00–05:59 |
| 6 | 30 | 06:00–08:59 |
| 6 | 500 | 09:00–09:59 |
| 6 | 30 | 10:00–10:59 |
| 6 | OFF | 11:00–11:59 |
| 6 | 30 | 12:00–13:59 |
| 6 | 500 | 14:00–14:59 |
| 6 | 30 | 15:00–15:59 |
| 6 | OFF | 16:00–16:59 |
| 6 | 30 | 17:00–18:59 |
| 6 | 500 | 19:00–19:59 |
| 6 | 30 | 20:00–22:59 |
| 6 | 30/110 | 23:00–23:59 |
| 7 | 30/110 | 00:00–05:59 |
| 7 | 30 | 06:00–08:59 |
| 7 | 500 | 09:00–09:59 |
| 7 | OFF | 10:00–10:59 |
| 7 | 30 | 11:00–13:59 |
| 7 | 500 | 14:00–14:59 |
| 7 | OFF | 15:00–15:59 |
| 7 | 30 | 16:00–18:59 |
| 7 | 500 | 19:00–19:59 |
| 7 | OFF | 20:00–20:59 |
| 7 | 500 | 21:00–21:59 |
| 7 | 30 | 22:00–22:59 |
| 7 | 30/110 | 23:00–23:59 |
| 8 | 30/110 | 00:00–05:59 |
| 8 | 30 | 06:00–08:59 |
| 8 | 500 | 09:00–09:59 |
| 8 | OFF | 10:00–10:59 |
| 8 | 30 | 11:00–13:59 |
| 8 | 500 | 14:00–14:59 |
| 8 | OFF | 15:00–15:59 |
| 8 | 30 | 16:00–18:59 |
| 8 | 500 | 19:00–19:59 |
| 8 | OFF | 20:00–20:59 |
| 8 | 30 | 21:00–22:59 |
| 8 | 30/110 | 23:00–23:59 |
| 9 | 30/110 | 00:00–05:59 |
| 9 | 30 | 06:00–08:59 |
| 9 | 500 | 09:00–09:59 |
| 9 | OFF | 10:00–11:59 |
| 9 | 30 | 12:00–13:59 |
| 9 | 500 | 14:00–14:59 |
| 9 | OFF | 15:00–16:59 |
| 9 | 30 | 17:00–18:59 |
| 9 | 500 | 19:00–19:50 |
| 9 | OFF | 20:00–20:59 |
| 9 | 30 | 21:00–22:59 |
| 9 | 30/100 | 23:00–23:59 |
| 10 | 30/100 | 00:00–05:59 |
| 10 | 30 | 06:00–08;59 |
| 10 | 500 | 09:00–09:59 |

For treatment of withdrawal symptoms from cocaine and amphetamines, somewhat higher frequencies are necessary including frequencies of up to 2000 Hz during some periods of time during day 1, during virtually all periods of time during days 2 through 5 and during less frequent periods of time during days 6 through 10.

In operating the apparatus of the invention, to carry out the methods of the invention described in the preceding paragraphs, the microprocessor 34 is initially preprogrammed to cause the device to automatically carry out the selected program from day one through day ten. The user does not, and cannot, vary the frequency of the pulses, their wave form or the time intervals at which the pulses are applied. The unit at all times maintains a constant current which is controlled by a potentiometer. Unlike many of the prior art devices, the device of the present invention maintains a constant current rather than a specified voltage.

The specific methods by which the microprocessor is programmed to carry out the methods of the invention are well understood by those skilled in the art and need not be discussed in detail herein. Similarly, the details of the circuitry of the apparatus and the method of constructing the circuitry depicted schematically in FIG. 3 is well within the skill of the art and need not be described in detail herein.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A method of alleviating pain and the symptoms of withdrawal of a patient during detoxification, comprising sequentially applying a multiplicity of electrical pulses to the patient's mastoid processes at a pulse repetition rate of between about 10 Hertz and about 300 Hertz, said electrical pulses being current controlled and being comprised of generally square waves having a pulse width of between approximately 100 and 300 microseconds, said electrical pulses being applied intermittently for about four days as follows:

(a) for two days and 23 hours at a frequency of 90 Hertz;

(b) for about 1 hour at a frequency of 300 Hertz;

(c) for about 22 hours at a frequency of 90 Hertz; and (d) for about 2 hours at a frequency of 300 Hertz.

2. A method of alleviating pain and the symptoms of withdrawal of a patient during detoxification, comprising sequentially applying a multiplicity of electrical pulses to the patient's mastoid processes at a pulse repetition rate of between about 10 Hertz and about 300 Hertz, said electrical pulses being current controlled and being comprised of generally square waves having a pulse width of between approximately 100 and 300 microseconds, said electrical pulses being applied intermittently as follows:

(a) for a first period of at least one day at a frequency of 90 Hertz;

(b) for a second period substantially less than said first period at a frequency of 300 Hertz;

(c) for a third period of at least three hours at a frequency of 90 Hertz; and (d) for a fourth period less than said third period at a frequency of 300 Hertz.

3. A method as defined in claim 2 in which said first period is greater than two days; said second period is less than one day; said third period is less than one day, but greater than said second period; and said fourth period is less than said third period.

* * * * *